US008323246B2

(12) United States Patent
Chiravuri et al.

(10) Patent No.: US 8,323,246 B2
(45) Date of Patent: Dec. 4, 2012

(54) DUAL DRUG DELIVERY DEVICE

(75) Inventors: Srinivas Chiravuri, Ann Arbor, MI (US); Allan Evans, Brighton, MI (US); Yogesh B. Gianchandani, Ann Arbor, MI (US); Jong M. Park, Plymouth, MN (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 12/810,286

(22) PCT Filed: Dec. 8, 2008

(86) PCT No.: PCT/US2008/085867
§ 371 (c)(1),
(2), (4) Date: Oct. 13, 2010

(87) PCT Pub. No.: WO2009/088608
PCT Pub. Date: Jul. 16, 2009

(65) Prior Publication Data
US 2011/0034872 A1    Feb. 10, 2011

Related U.S. Application Data

(60) Provisional application No. 61/018,607, filed on Jan. 2, 2008.

(51) Int. Cl.
*A61M 37/00* (2006.01)
(52) U.S. Cl. ............................................. 604/132
(58) Field of Classification Search .................. 604/132, 604/890.1, 891.1
See application file for complete search history.

(56) References Cited

U.S. PATENT DOCUMENTS
4,772,263 A * 9/1988 Dorman et al. ............... 604/132
(Continued)

FOREIGN PATENT DOCUMENTS
WO          WO 97/42998          11/1997

OTHER PUBLICATIONS

A. Evans, J.M. Park, R.P. Taylor, T.R. Brosten, G.F. Nellis, S.A. Klein, J.R. Feller, L. Salerno and Y.B. Gianchandani, "A Low Power, Micromachined Proportional Valve for Drug Delivery," The Tenth International Conference Miniaturized Chemical and Biochemical Analysis Systems (MicroTAS 2006), Tokyo, Nov. 5-9, 2006.*

(Continued)

*Primary Examiner* — Nicholas D Lucchesi
*Assistant Examiner* — Aarti B Berdichevsky
(74) *Attorney, Agent, or Firm* — Marshall, Gerstein & Borun LLP

(57) ABSTRACT

A liquid delivery apparatus for the intrathecal delivery of one or more medications to a patient is disclosed. The liquid delivery apparatus generally includes a liquid reservoir, a liquid metering unit fluidly connected to the liquid reservoir, and a catheter delivery tube fluidly connected to the liquid metering unit. Preferably, the liquid delivery apparatus includes two or more liquid reservoirs. In various embodiments, the liquid reservoir includes a deformable balloon and a compressive sleeve spring as a pressure source, the liquid metering unit is a piezoelectrically actuated microvalve, and/or diagnostic sensors are included in the apparatus. The disclosed apparatus are compact, volume-efficient, energy-efficient, capable of delivering accurate fluid volumes, and address problems associated with multi-medication therapies. Methods of operating the liquid delivery apparatus are also disclosed.

28 Claims, 8 Drawing Sheets

U.S. PATENT DOCUMENTS

| | | | |
|---|---|---|---|
| 5,163,909 | A | 11/1992 | Stewart |
| 5,785,688 | A * | 7/1998 | Joshi et al. .................. 604/141 |
| 6,048,328 | A * | 4/2000 | Haller et al. ............. 604/288.03 |
| 6,554,822 | B1 * | 4/2003 | Holschneider et al. .... 604/892.1 |
| 6,619,123 | B2 | 9/2003 | Gianchandani et al. |
| 6,666,845 | B2 | 12/2003 | Hooper et al. |
| 7,083,593 | B2 * | 8/2006 | Stultz .............................. 604/65 |
| 7,092,753 | B2 * | 8/2006 | Darvish et al. .................. 604/21 |
| 7,789,371 | B2 | 9/2010 | Gianchandani et al. |
| 2002/0156462 | A1 * | 10/2002 | Stultz ........................ 604/891.1 |
| 2006/0206054 | A1 | 9/2006 | Shekalim |

OTHER PUBLICATIONS

C. R. Neagu, et al., "An Electrochemical Microactuator: Principle and First Results," *J. Microelectromechanical Sys.*, 5(1) (Mar. 1996).

P. S. Tumber, et al., "The Control of Severe Cancer Pain by Continuous Intrathecal Infusion and Patient Controlled Intrathecal Analgesia with Morphine, Bupivacaine and Clonidine," *Pain*, 78:217-20 (Dec. 1998).

W. A. Visser, "Combined Spinal Epidural Anaesthesia," *Anaesthesia*, 54:299-300 (Mar. 1999).

T. J. Smith et al., "Pain Management, Including Intrathecal Pumps," *Curr. and Pain Headache Rep.*, 9:243-48 (Aug. 2005).

A. T. Evans, et al., "A Low Power, Microvalve-Regulated Drug Delivery System Using a Si Micro-Spring Pressurized Balloon Reservoir," *Transducers & Eurosensors*, 10-14:359-362 (Jun. 2007).

K. H. Knight, et al., "Implantable Intrathecal Pumps for Chronic Pain: Highlights and Updates, " *Croat. Med. J.*, 48:22-34 (2007).

S. Li, et al., "A Single Cell Electrophysiological Analysis Device with Embedded Electrode," *Sensors and Actuators* A(Physical), 134:20-6 (2007).

M. Carmichael, "The Changing Science of Pain," *Newsweek*, 149:40-47 (Jun. 4, 2007).

A. T. Evans, et al., "Dual Drug Delivery Device for Chronic Pain Management Using Micromachined Elastic Metal Structures and Silicon Microvalves," *Micro Electro Mechanical Systems*, pp. 252-255 (Jan. 2008).

International Preliminary Report on Patentability and Written Opinion of the International Searching Authority in counterpart International Application No. PCT/US2008/085867, dated Jul. 6, 2010.

International Search Report for International Application No. PCT/US2008/085867, dated Jul. 9, 2009.

Written Opinion of the International Searching Authority, International Application No. PCT/US2008/085867, dated Jul. 9, 2009.

* cited by examiner

DUAL DRUG DELIVERY DEVICE

CROSS REFERENCE TO RELATED APPLICATION

This application claims the benefit of U.S. provisional patent application Ser. No. 61/018,607 filed Jan. 2, 2008, the disclosure of which is incorporated herein by reference, is claimed.

STATEMENT REGARDING FEDERALLY SPONSORED RESEARCH

Research relating to the claimed subject matter was supported in part by the United States government under Grant No. NNA05CP85G awarded by the National Aeronautics and Space Administration. The government may have certain rights in the claimed subject matter.

BACKGROUND

The disclosure generally relates to liquid delivery apparatus and, more specifically, to implantable drug delivery devices. Implantable drug delivery devices are medical devices used to administer an infusate (e.g., medications/drugs, chemicals, solutions) to a predefined location in a patient (e.g., intrathecal delivery). The devices can be used to treat chronic pain, spasticity, or other medical conditions that would benefit from controlled administration of an infusate.

Chronic pain is a persistent condition in which the source of the pain cannot be treated. It afflicts an estimated 100 million people in the United States with annual costs exceeding $100 billion. W. A. Visser, "Combined spinal epidural anaesthesia," *Anaesthesia*, vol. 54, p. 300, March 1999. It is often a symptom of incurable or intractable conditions like cancer, but it can also arise from severe trauma, limb loss, or other combat-related injuries. P. S. Tumber et al., "The control of severe cancer pain by continuous intrathecal infusion and patient controlled intrathecal analgesia with morphine, bupivacaine and clonidine," *Pain*, vol. 78, pp. 217-220, December 1998; M. Carmichael, "The changing science of pain," *Newsweek*, vol. 149, pp. 40-47, Jun. 4, 2007; T. J. Smith et al., "Pain management, including intrathecal pumps," *Curr. Pain Headache Rep.*, vol. 9, pp. 243-248, August 2005. If the chronic pain condition is severe, it may be treated with surgery, spinal cord stimulation, or the implantation of an intrathecal drug pump.

The technological aspects of intrathecal drug pumps have remained relatively unchanged for over a decade. Conventional intrathecal pumps consist of a battery-powered, programmable pump which is connected to or incorporates an infusate reservoir. The pump is implanted under tissue in the patient's abdomen and connected to a catheter that continues to a infusion/drug delivery point (e.g., a spinal entry point). K. Knight, "Implantable Intrathecal Pumps for Chronic Pain: Highlights and Updates," *Croat. Med. J.*, vol. 48, pp. 22-34, 2007.

In some intrathecal pumps, an electrically powered mechanism pumps the infusate from the reservoir to the infusion point. Such pumps can be used to control the dosage of the infusate and variable dosing protocols can be followed.

In other intrathecal pumps, the infusate is driven to the infusion point by a propellant exerting a positive and constant pressure on the infusate reservoir. Such devices require large rigid housings to contain both the infusate reservoir and the propellant. While such gas-driven pumps can be cost-effective, they suffer from infusate delivery problems when environmental factors change the pressure that the propellant exerts on the infusate reservoir.

The problem of variable flow in gas-driven pumps has been addressed using drive-spring diaphragms, for example as disclosed in U.S. Pat. No. 6,666,845. In such systems, a drive spring provides the constant pressure to collapse the infusate reservoir. Similar to the gas-driven pumps, the spring-driven pumps require a large and rigid housing.

A limitation of commercially available intrathecal pumps is that they provide only a single infusate reservoir, while preferred methods for pain management specify the administration of multiple medications with different dosing and delivery protocols. However, such single-reservoir systems require drugs to be mixed in a fixed ratio and dispensed from a single reservoir, which can be problematic with drugs that are incompatible and/or unstable when stored in a mixture for an extended period. Moreover, single-reservoir systems cannot independently control the relative flow rates of individual drugs.

The large, rigid nature of conventional intrathecal pumps limits the applicability of the technology. The utility of an intrathecal device can be represented by its volume efficiency. The volume efficiency is the ratio of the volume of the infusate reservoir when full to the volume of the entire intrathecal pump device. As the volume efficiency is limited by the architecture of the pump and its component sizes, improvements in volume efficiency in conventional intrathecal pumps is limited. A low volume efficiency can restrict the use of intrathecal pumps, for example preventing their use in pediatric applications, which require a significantly smaller pump than that which can be used in an adult.

Thus, there is need for an intrathecal drug delivery device that has a high volume efficiency, is volume-scalable, and can independently deliver multiple drugs.

SUMMARY

This need is addressed by the design and use of an inventive liquid delivery apparatus. The apparatus generally include one or more liquid reservoirs, a liquid metering unit fluidly connected to each liquid reservoir, and a catheter delivery tube fluidly connected to the liquid metering unit(s). The disclosed apparatus arc compact, volume-efficient, energy-efficient, and capable of delivering accurate fluid flow rates/volumes. When the liquid delivery apparatus include two or more fluid reservoirs, the fluid flow rate from each reservoir can be independently controlled, and complications due to medication incompatibilities can be avoided.

In an embodiment, a liquid delivery apparatus includes a liquid delivery pathway, the liquid delivery pathway including a liquid reservoir, a liquid metering unit fluidly connected to the liquid reservoir, and a catheter delivery tube fluidly connected to the liquid metering unit. The liquid reservoir further includes a deformable balloon and a pressure source selected from the group consisting of a compressive sleeve spring and an electrolytic fluid cell. Preferably, the liquid delivery apparatus includes two or more liquid delivery pathways. Preferably, the liquid metering unit includes a throttle, and the liquid delivery pathway further includes a means for measuring the volume of the liquid reservoir (e.g., a pressure sensor fluidly connected to the liquid reservoir between the liquid reservoir and the liquid metering unit throttle). More preferably, the liquid delivery apparatus includes a liquid delivery control module having a microprocessor electrically connected to the throttle and the means for measuring the volume of the liquid reservoir and a battery electrically connected to the microprocessor. When the liquid delivery apparatus includes two or more liquid delivery pathways, if it preferable for the microprocessor to be capable of independently controlling liquid flow through each liquid delivery pathway. The throttle can be a piezoelectrically actuated microvalve, in which case the microvalve preferably includes a first plate (e.g., a silicon-on-insulator substrate) and a second plate (e.g., glass) spaced apart and joined together to define a flow path having an inlet fluidly connected to the liquid reservoir and an outlet fluidly connected to the catheter delivery tube and a piezoelectric material (e.g., lead zirconium titanate) external to the flow path and in contact with the first plate. The compressive sleeve spring is preferably made from a piezoresistive material, for example an alloy of copper, chromium, and nickel. Optionally, the liquid delivery apparatus can include various access ports, for example a refill port for the liquid reservoir and/or a bolus port for the catheter delivery tube.

In another embodiment, a liquid delivery apparatus includes a plurality of liquid delivery pathways, where each liquid delivery pathway includes a liquid reservoir, a piezoelectrically actuated microvalve fluidly connected to the liquid reservoir, and a catheter delivery tube fluidly connected to the piezoelectrically actuated microvalve. The microvalve preferably includes a first plate (e.g., a silicon-on-insulator substrate) and a second plate (e.g., glass) spaced apart and joined together to define a flow path having an inlet fluidly connected to the liquid reservoir and an outlet fluidly connected to the catheter delivery tube and a piezoelectric material (e.g., lead zirconium titanate) external to the flow path and in contact with the first plate. Preferably, the liquid delivery pathway further includes a means for measuring the volume of the liquid reservoir (e.g., a pressure sensor fluidly connected to the liquid reservoir between the liquid reservoir and the liquid metering unit throttle). The liquid reservoir can include a deformable balloon and a pressure source selected from a compressive sleeve spring (e.g., a copper, chromium, and nickel alloy), a torsion spring, and an electrolytic fluid cell. Preferably, the liquid delivery apparatus includes a liquid delivery control module having a microprocessor electrically connected to the piezoelectrically actuated microvalve and the means for measuring the volume of the liquid reservoir for each of the liquid delivery pathways and a battery electrically connected to the microprocessor.

In yet another embodiment, a liquid delivery apparatus includes a liquid delivery pathway and a sensor selected from the group consisting of a flow meter fluidly connected to the liquid delivery pathway, an accelerometer, and combinations thereof. The liquid delivery pathway further includes a liquid reservoir, a liquid metering unit fluidly connected to the liquid reservoir, and a catheter delivery tube fluidly connected to the liquid metering unit. Preferably, the liquid delivery apparatus includes two or more liquid delivery pathways, and the sensor includes an accelerometer (e.g., a shock senor or a plurality of shock sensors). The liquid reservoir can include a deformable balloon and a pressure source selected from a compressive sleeve spring, a torsion spring, and an electrolytic fluid cell, the liquid metering unit can include a throttle, and the liquid delivery pathway can include a means for measuring the volume of the liquid reservoir (e.g., a pressure sensor fluidly connected to the liquid reservoir between the liquid reservoir and the liquid metering unit). Preferably, the liquid delivery apparatus includes a liquid delivery control module having a microprocessor electrically connected to the throttle and the means for measuring the volume of the liquid reservoir and a battery electrically connected to the microprocessor.

In another embodiment, a liquid delivery apparatus includes a liquid reservoir including a deformable balloon having an interior volume and at least one deformable interior wall in the interior volume, such that the at least one deformable interior wall defines a plurality of reservoir chambers in the interior volume. The liquid delivery apparatus further includes a plurality of liquid metering units, each of which is fluidly connected to one of the reservoir chambers, and a plurality of catheter delivery tubes, each of which is fluidly connected to one of the liquid metering units. Preferably, the liquid reservoir further includes a pressure source selected from a compressive sleeve spring, a torsion spring, and an electrolytic fluid cell; each liquid metering unit includes a throttle; and, the liquid delivery apparatus includes a means for measuring the volume of the liquid remaining in the reservoir chambers. The liquid delivery apparatus preferably also includes a liquid delivery control module having a microprocessor electrically connected to the throttle and the means for measuring the volume of the liquid remaining in the reservoir chambers and a battery electrically connected to the microprocessor.

For any of the disclosed liquid delivery apparatus having two or more liquid reservoirs, methods of delivering a plurality of medications to a patient in need thereof are disclosed. The methods generally include providing the liquid delivery apparatus with a microprocessor electrically connected to the liquid metering units and, optionally, a means for measuring the volumes of the liquid reservoirs. The liquid delivery apparatus is then charged with a plurality of medications, such that at least one liquid reservoir contains a medication that is different from the medication contained in another liquid reservoir. Finally, the plurality of medications is delivered the patient at independently controlled flow rates by independently adjusting each liquid metering unit in response to a flow control program stored in the microprocessor.

For the disclosed liquid delivery apparatus having two or more liquid reservoirs and an accelerometer, a method of optimizing the dosage level of a plurality of medications to a patient in need thereof is disclosed. The method includes charging the liquid delivery apparatus with the plurality of medications, wherein at least one liquid reservoir contains a first medication that is different from a second medication contained in another liquid reservoir; monitoring a first activity level of the patient to identify a first optimum dosage level of the first medication; monitoring a second activity level of the patient to identify a second optimum dosage level of the second medication; and, delivering to the patient the first medication at the first optimum dosage level and the second medication at the second optimum dosage level. Preferably, the step of monitoring the first activity level includes delivering only the first medication to the patient at a plurality of first dosage levels, each of the first dosage levels being delivered for a preselected length of time; measuring the first activity level of the patient at each of the first dosage levels using the accelerometer; and, selecting the first optimum dosage level based on the first dosage level that provides the greatest first activity level. Similarly, the step of monitoring the second activity level includes delivering only the second medication to the patient at a plurality of second dosage levels, each of the second dosage levels being delivered for a preselected length of time; measuring the second activity level of the patient at each of the second dosage levels using the accelerometer; and, selecting the second optimum dosage level based on the second dosage level that provides the greatest second activity level.

BRIEF DESCRIPTION OF THE DRAWINGS

For a more complete understanding of the disclosure, reference should be made to the following detailed description and accompanying drawings wherein.

Figure 1:
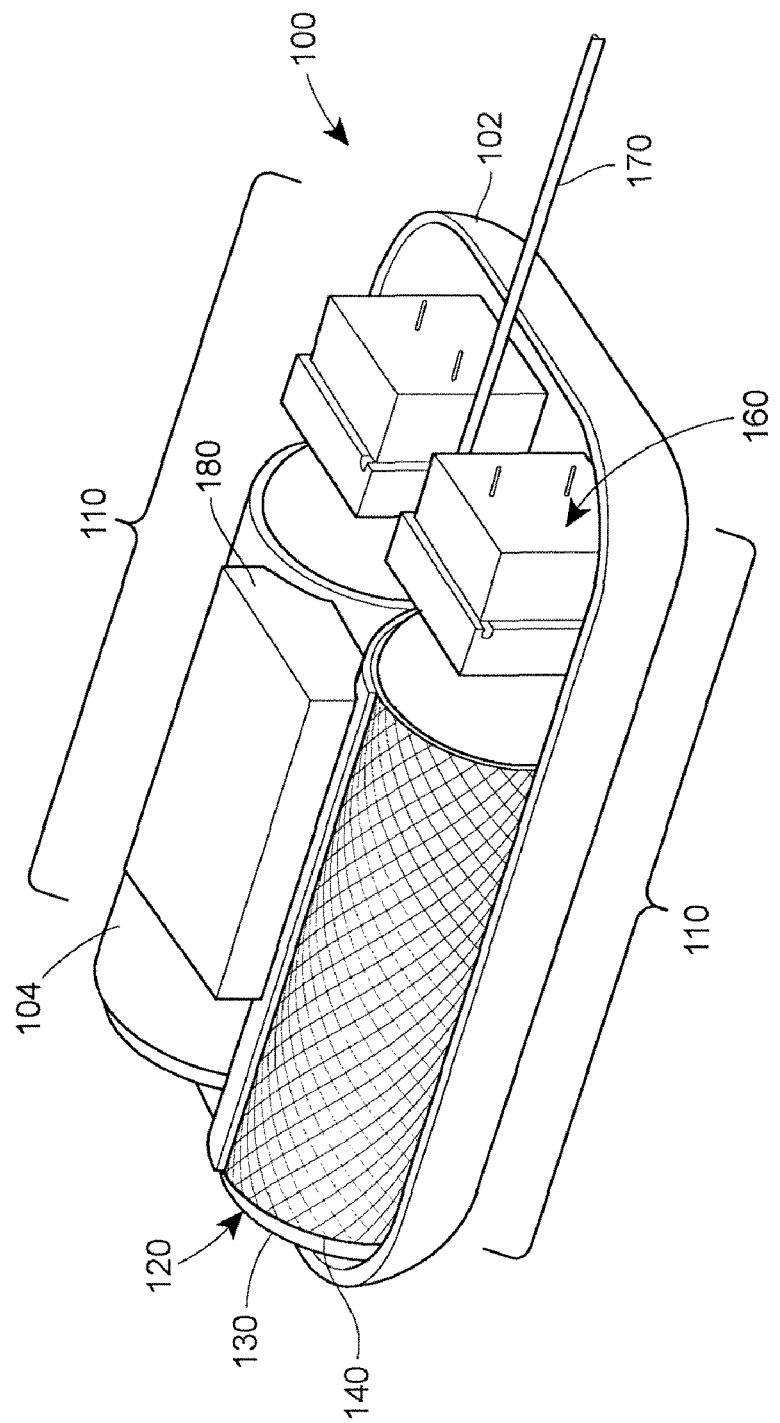
FIG. 1 is a perspective view of a liquid delivery apparatus according to an embodiment of the disclosure.

While the disclosed process and apparatus are susceptible of embodiments in various forms, specific embodiments of the invention are illustrated in the drawings (and will hereafter be described) with the understanding that the disclosure is intended to be illustrative, and is not intended to limit the invention to the specific embodiments described and illustrated herein.

DETAILED DESCRIPTION

Figure 2:
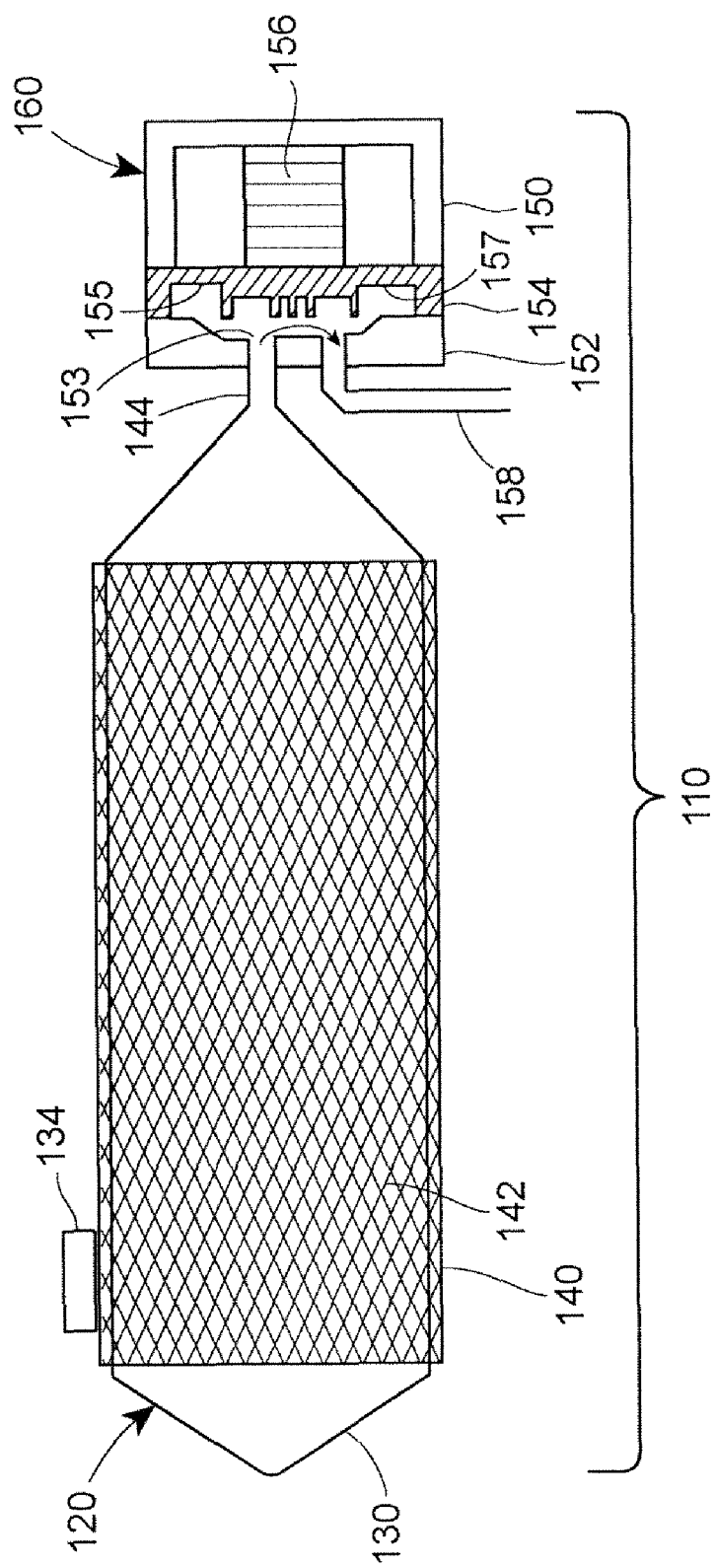
FIG. 2 is aside view of a liquid delivery pathway in the liquid delivery apparatus of FIG. 1.

Disclosed herein are liquid delivery apparatus and processes using the same. One embodiment of a liquid delivery apparatus 100 is illustrated in FIGS. 1 and 2. As illustrated, the liquid delivery apparatus 100 includes two liquid delivery pathways 110 encased in an external housing 102, although some embodiments can include a single liquid delivery pathway or more that two liquid delivery pathways. The external housing 102 is preferably made from any rigid, biocompatible material, for example a metal (e.g., titanium, aluminum, stainless steel) or a rigid, durable plastic. Each liquid delivery pathway 110 generally includes a reservoir 120 containing a fluid that is enclosed by an internal housing 104 (which can be made from the same or different material as the external housing 102) and is fluidly connected to a liquid metering unit 160. The outlet of each liquid metering unit 160 is preferably fluidly connected to a single liquid delivery catheter 170. The liquid delivery catheter 170 can be a single-lumen catheter, in which case the fluids being delivered mix upon exiting the liquid metering unit 160. Alternatively, the liquid delivery catheter 170 can be a multi-lumen catheter, in which case the fluids being delivered remain segregated at least until they reach the delivery site in a patient's body. The liquid delivery catheter 170 can include a bolus port (e.g., an access line to the catheter sealed with a septum or other re-sealable structure; not shown) allowing manual injection of a medication directly into the patient, bypassing the liquid delivery apparatus 100. Preferably, the liquid delivery apparatus 100 also includes a liquid delivery control module 180 to independently control each of the two liquid delivery pathways 110.

The liquid delivery apparatus 100 is preferably both compact and volume-efficient. Because the liquid delivery apparatus 100 is intended for implantation into a human patient, the device should be as small as practical for aesthetic purposes, for patient comfort, and to minimize the invasiveness of the implantation procedure. For adult human patients, the liquid delivery apparatus 100 preferably has a total volume of about 120 ml or less, more preferably about 90 ml or less, and most preferably about 80 ml or less. Because the liquid delivery apparatus 100 can be scaled down for pediatric applications, smaller total volumes are contemplated. For example, the liquid delivery apparatus 100 preferably has a total volume ranging from about 20 ml to about 120 ml, about 30 ml to about 90 ml, or about 40 ml to about 80 ml. Relatively small total volumes are possible because the liquid delivery apparatus 100 is relatively volume-efficient, meaning that a substantial portion of the total device volume is allocated to the reservoir(s) 120 and that the liquid delivery apparatus 100 can be operated at longer intervals between refilling the reservoir(s) 120. For example, the liquid delivery apparatus 100 preferably has a volume efficiency of at least 0.35, more preferably at least about 0.4 or at least about 0.5, for example in a range of about 0.4 to about 0.8 or about 0.4 to about 0.6.

Various elements, embodiments, and the operation of the disclosed liquid delivery apparatus are described in more detail below.

Liquid Reservoirs

The reservoir 120 is not particularly limited and can include any structure that is able to both retain and release its fluid contents. Generally, the reservoir 120 is designed so that it contracts and expands with the discharge and refilling, respectively, of its fluid contents. Suitable reservoir structures include deformable balloons, diaphragms, and expanding bellows. A swollen hydrogel also can serve as a suitable reservoir structure, being able to discharge its absorbed contents in response to an external pressure, for example when encased in an enclosure used to direct the output of the discharged contents. Fluid being delivered from the reservoir 120 exits via an outlet 144 (e.g., a piece of flexible tubing fluidly connecting the reservoir 120 to the liquid metering unit 160). The reservoir 120 preferably includes a refill port 134 (e.g., a septum or other re-sealable structure) allowing access to the reservoir 120 for recharging a depleted fluid reserve.

Preferably, the reservoir 120 includes a deformable balloon 130, for example an inflatable structure like those used in balloon angioplasty treatments. The deformable balloon 130 can be made from any flexible, liquid-impermeable material, for example elastomeric polymers, with polyethylene terephthalate (PET) being a particularly preferred material. Preferably, the elasticity of the deformable balloon 130 creates a pressure within the balloon 130 when the balloon 130 is filled with a liquid and expands, which pressure should be sufficient to drive the liquid through the outlet 144 in the balloon 130. Still further, the pressure supplied by the balloon 130 preferably does not significantly vary between different discharge/refill cycles of the balloon 130, such that is the balloon 130 has a repeatable, known relationship for reservoir pressure as a function of reservoir volume. P(V).

The reservoir 120 preferably also includes a pressure source 140 to discharge fluid from the reservoir 120. In some embodiments, the reservoir 120 itself may provide the necessary pressure driving source to discharge fluid from the reservoir 120 (e.g., when the reservoir 120 includes the elastic, deformable balloon 130). In other embodiments, the liquid metering unit 160 may provide a suction pressure (e.g., when it includes a pump) sufficient to withdraw fluid from the reservoir 120 at a controlled rate. However, it is often preferable to include the pressure source 140 to provide a positive, controlled discharge pressure. Suitable pressure sources 140 are not particularly limited, for example including springs (e.g., compression sleeve springs and torsion springs, described in more detail below), electrolytic fluid cells (e.g., using a liquid that vaporizes to form a pressurizing gas bubble in response to a current passed through the liquid), thermal fluid cells (e.g., using a liquid that vaporizes to form a pressurizing gas at physiological temperatures), swollen hydrogels, and gaseous propellants. The use of electrolytic and thermal fluid cells to generate bubbles for pumping action is known, for example as described in Neagu, et al. "An electrochemical microactuator: principle and first results," *J. Microelectromechanical Sys.*, 5(1), March 1996 pp. 2-9 and S. Li, et al. "A single cell electrophysiological analysis device with embedded electrode," *Sensors and Actuators A* (Physical), v. 134, n. 1, Feb. 28, 2007, p. 20-6, both of which are herein incorporated by reference.

When the reservoir 120 has a deformable construction, the pressure source 140 can simply act externally to the reservoir 120 to compress and contract the reservoir 120 while expelling the fluid contents thereof. When the reservoir 120 has an at least partially rigid construction with a deformable or slidable boundary between the fluid contents of the reservoir 120 and the pressure source 140, the pressure source 140 can be used to push against the deformable or slidable boundary to expel the fluid contents of the reservoir 120 (e.g., a rigid tubular reservoir 120 having a slidable diaphragm opposite the reservoir outlet 144).

As illustrated in FIGS. 1 and 2, a preferred pressure source 140 is a compressive sleeve spring 142. The compressive sleeve spring 142 is a cylindrical spring in which the spring acts to provide a radially inward compressive force. Thus, when the compressive sleeve spring 142 ensleeves a tubular shaped reservoir 120 (e.g., the deformable balloon 130 as illustrated), the spring's compressive force provides the pressure to expel fluid from the reservoir 120. Preferably, the compressive sleeve spring 142 is made from a metal alloy that is biocompatible, corrosion resistant, durable, and/or has favorable electrical properties. An example of a suitable metal alloy is a Co/Cr/Ni alloy that is commercially available under the name ELGILOY (available from Elgiloy Specialty Metals, Elgin, Ill.). The compressive sleeve spring 142 can be formed by laminating a sheet of the Co/Cr/Ni alloy with photoresist, patterning the photoresist, and then chemically etching the alloy sheet. The etched alloy sheet is then rolled and fixed into a cylindrical shape to form the compressive sleeve spring 142.

Figure 3A:
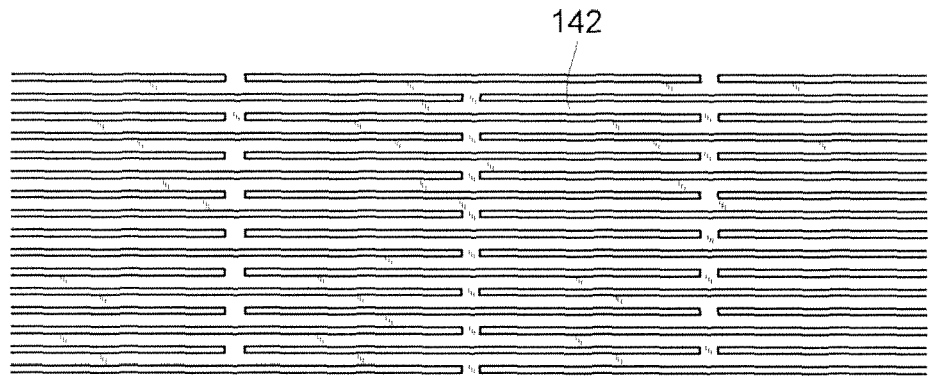
FIGS. 3*a* to 3*d* are views of a compressive sleeve spring and a deformable balloon in the liquid delivery apparatus of FIG. 1.
Figure 3B:
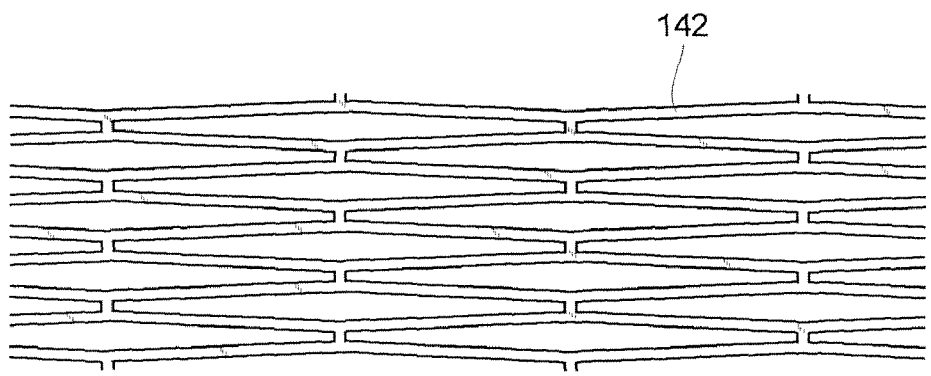
Figure 3C:
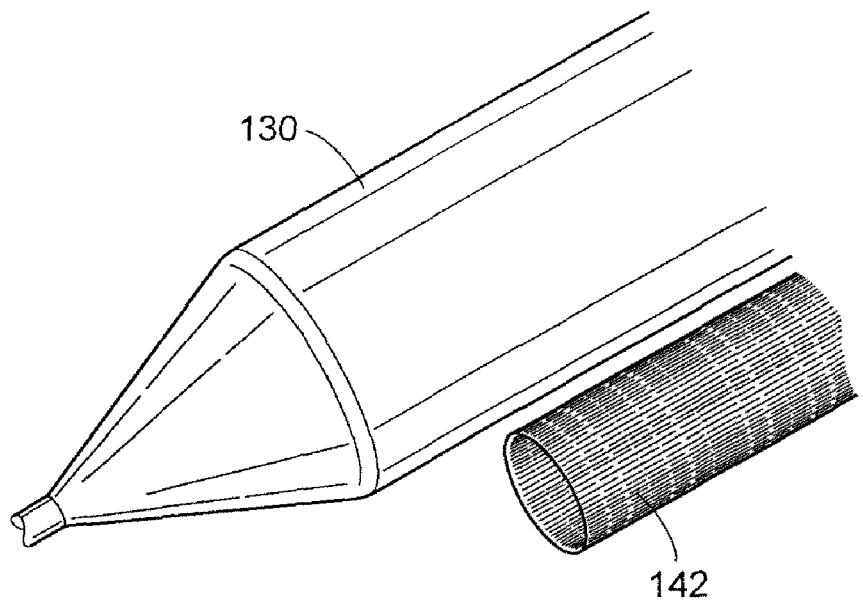
Figure 3D:
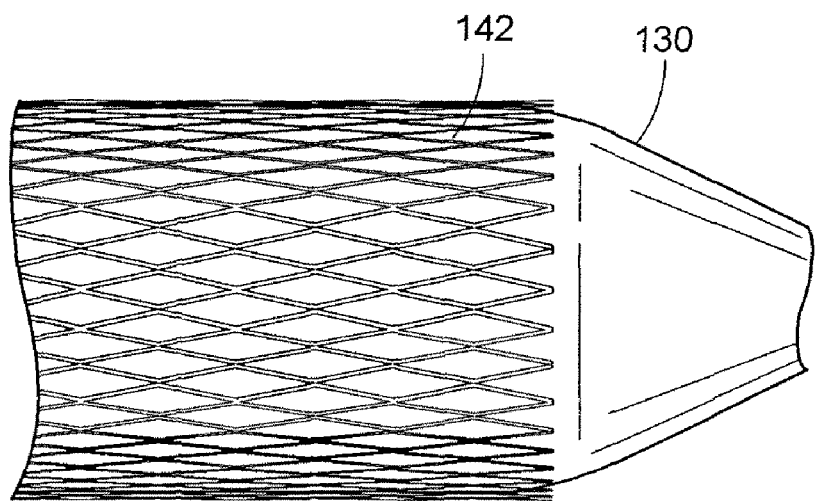

FIGS. 3a-3d illustrate the compressive sleeve spring 142 in various stages. FIGS. 3a and 3b show the compressive sleeve spring 142 as the etched alloy sheet, in a relaxed and stretched state, respectively. FIG. 3c illustrates an 18.8 ml inflated deformable balloon 130 and a relaxed compressive sleeve spring 142, while FIG. 3d illustrates the same deformable balloon 130 and compressive sleeve spring 142 in an ensleeved configuration. In the embodiment shown in FIGS. 3a-3d, the springs are 100 μm thick, the spring beams are 150 μm wide, the mesh cell size is 600 μm×6 mm, and the compressive sleeve spring 142 was formed from a 60 mm×10 mm etched alloy sheet.

Similar to the deformable balloon 130, the compressive sleeve spring 142 preferably provides a repeatable pressure-volume profile between subsequent discharge/refill cycles. That is, after the compressive sleeve spring 142 is conditioned (i.e., strained in the first instance), the spring constant for the radial compressive force of the compressive sleeve spring 142 is substantially constant and repeatable.

Figure 4:
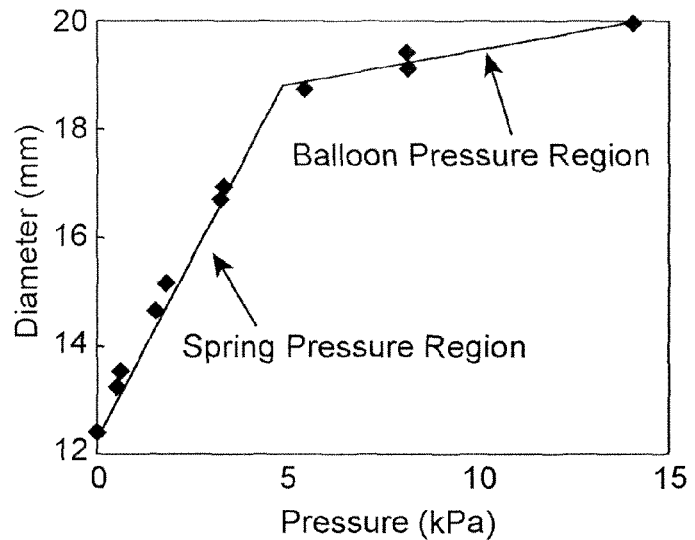
FIG. 4 is graph illustrating the relationship between the applied pressure and the diameter of a reservoir in the liquid delivery apparatus of FIG. 1.

The repeatable pressure-volume profile of both the deformable balloon 130 and the compressive sleeve spring 142 allows the determination of the reservoir 120 volume by measuring the reservoir 120 pressure. By extension, pressure measurements at multiple time intervals permits determination of the flow rate of fluid exiting the reservoir 120. FIG. 4 illustrates a representative pressure-volume profile for the balloon 130/spring 142 embodiment of FIG. 3d. Specifically, FIG. 4 plots the diameter of a cylindrical deformable balloon 130 (i.e., which correlates directly to the reservoir 120 volume (specifically, the volume of the fluid remaining in the reservoir 120)) as a function of the net pressure applied by the combination of the deformable balloon 130 and the compressive sleeve spring 142. At low volumes, the balloon 130 diameter changes linearly with a high slope (e.g., from 12 mm to 19 mm as illustrated) as the compressive sleeve spring 142 provides the dominant pressurizing force. At higher volumes (e.g., above 19 mm as illustrated), the elasticity of the balloon 130 material begins to dominate the pressure generation curve. When fully charged, the illustrated deformable balloon 130 is about 20 mm in diameter and the reservoir 120 generates almost 15 kPa of pressure. Because the relationship illustrated in FIG. 4 is a continuous, single-valued function, any measured reservoir 120 pressure can be correlated with a unique reservoir 120 volume.

In other embodiments, the distention of the compressive sleeve spring 142 and its rate of change can be directly measured to determine the reservoir 120 volume and exiting fluid flow rate. Knowledge of the compressive sleeve spring 142 distention correlates to the reservoir 120 diameter and, thus, also the reservoir volume. In such embodiments, the compressive sleeve spring 142 preferably is made from a piezoresistive material. Piezoresistive materials display measurable changes in the electrical resistance of the material based on its deformation (e.g., an increase in the cylindrical cross section of the compressive sleeve spring 142). This effect provides a direct method to measure the compressive sleeve spring 142 expansion and, thus, the volume of the reservoir 120. Similarly, by measuring the rate of change in the resistance of the piezoresistive material, the flow rate of fluid exiting the reservoir 120 also can be determined.

In another embodiment (not shown) the pressure source 140 is applied to the reservoir 120 by a torsion spring (not shown). The torsion spring is a multiplicity of springs in parallel that apply force to the deformable balloon 130 at different axial locations along the length of the deformable balloon 130. In a refinement, the torsion spring does not apply an equal force at all axial locations of the deformable balloon 130; the individual springs further from the outlet 144 of the deformable balloon 130 are stiffer (i.e., they apply more force) than the springs near the outlet 144. The resulting force gradient in this embodiment the deformable balloon 130 empties from the point furthest from the outlet 144 first, similar to a tube of toothpaste.

Figure 5A:
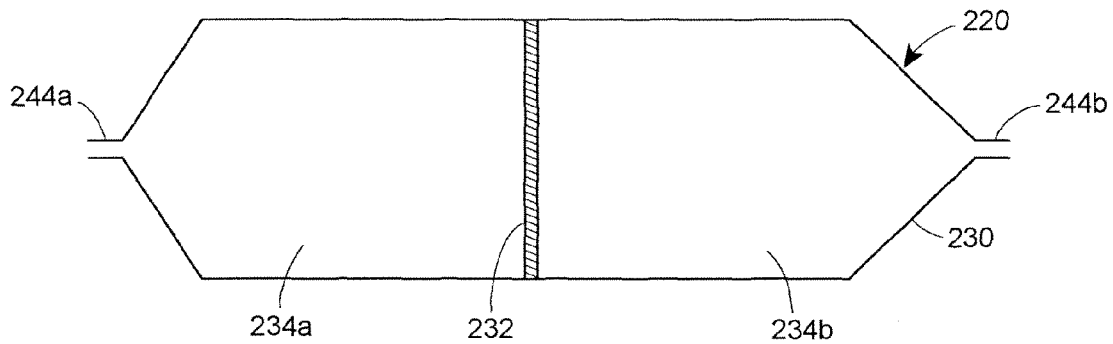
FIGS. 5*a* and 5*b* are side views of an alternate embodiment of a reservoir for a liquid delivery apparatus.
Figure 5B:
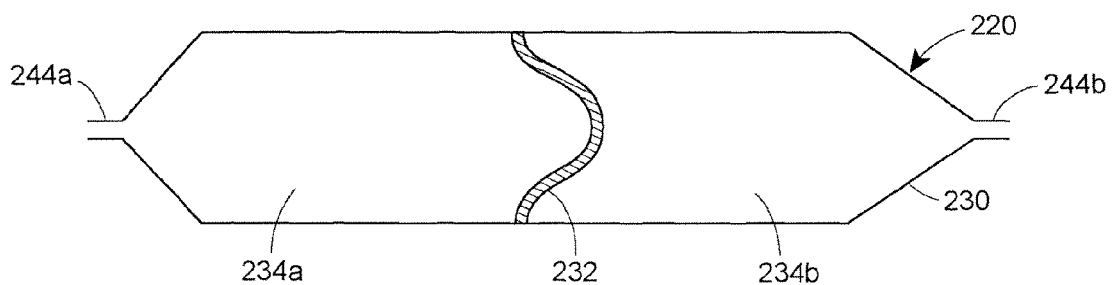

FIGS. 5a and 5b illustrate an alternate embodiment in which the two liquid reservoirs 120 from FIG. 1 are replaced with a single liquid reservoir 220 having two reservoir chambers 234a, 234b. The reservoir 220 includes a deformable balloon 230 (similar in construction to the deformable balloon 130 described above) that has a deformable interior wall 232 defining the reservoir chambers 234a, 234b in the interior volume of the deformable balloon 230. The reservoir 220 also includes outlets 244a, 244b for each of the reservoir chambers 234a, 234b, each of which is fluidly connected to its own liquid metering unit (not shown). In general, any pressure source can be used to expel fluid from the reservoir chambers 234a, 234b, although a compressive sleeve spring (not shown) is preferred. The deformable interior wall 232 allows fluid to be withdrawn from the reservoir chambers 234a, 234b at different rates, even though only a single reservoir 220 and single pressure source is used. Specifically, as the compressive sleeve spring (or other pressure source) expels liquid from the reservoir 220, independent liquid metering units downstream from the outlets 244a, 244b can be used to withdraw fluid from the reservoir chambers 234a, 234b at different rates because the interior wall 232 can deform to accommodate an uneven volume distribution between the fluids remaining in the reservoir 220. For example, as illustrated in FIG. 5b, the net flow of fluid of out the reservoir chamber 234b is larger than that out of the reservoir chamber 234a, and thus the interior wall 232 deflects to the right so that the volume of the reservoir chamber 234b (volume of the fluid remaining in the reservoir chamber 234b) is less than that of the reservoir chamber 234a.

Liquid Metering Units

The liquid metering unit 160 fluidly connected to each reservoir 120 is not particularly limited and can include any structure or device that is capable of controlling the flow rate of fluid exiting the reservoir 120. When the reservoir 120 includes a pressure source 140 to actively expel fluid from the reservoir 120, the liquid metering unit 160 can simply include structure that attenuates the flow rate, for example a throttle (e.g., a piezoelectrically actuated microvalve), a valve (e.g., mono-, bi-, multi-stable), or a flow restrictor (e.g., a grooved plate, capillary tubing, an etched flow chip). In the absence of a pressure source 140, the liquid metering unit 160 preferably includes a pump to actively withdraw fluid from the reservoir 120. A variety of pumps are suitable, including, for example, peristaltic pumps (e.g., those having a variable reservoir controlled by a valve at its inlet and outlet such that the upstream valve opens as the reservoir volume increases, and the downstream valve opens as the reservoir volume reduces), magnetically-driven motor pumps, magnetohydrodynamic-based pumps, electrohydrodynamic-based pumps, ultrasonically actuated pumps, and electro-osmotically actuated pumps. The liquid metering unit 160 also can include a mixer (static or otherwise; not shown) either upstream of the liquid metering unit 160 (e.g., in an embodiment where two or more reservoirs 120 feed fluid to a single liquid metering unit 160) or downstream of the liquid metering unit 160 (e.g., in an embodiment where it is desirable to actively mix the fluids exiting two or more liquid metering units 160). In any of the above embodiments, various liquid metering units 160 (e.g., throttles, valves, pumps) can be combined in series or in parallel depending on a particular fluid delivery application.

Preferably, the liquid metering unit 160 includes a throttle 150 providing a variable hydraulic resistance so that a continuum of fluid flow rates exiting from the reservoir 120 is possible. A preferred throttle 150 is a piezoelectrically actuated microvalve (PAM), for example as illustrated in FIG. 2 and as described in more detail in U.S. patent application Ser. No. 11/756,342 (filed May 31, 2007), the entire disclosure of which is incorporated herein by reference.

As illustrated in FIG. 2, the PAM throttle 150 includes a first plate 154 and a second plate 152 spaced apart and joined together to define a flow path 153 having inlet fluidly connected to the liquid reservoir 120 (i.e., the outlet 144 as illustrated) and an outlet catheter delivery tube 158 that is fluidly connected to the liquid delivery catheter 170 (illustrated in FIG. 1). The first plate 154 is preferably a silicon-on-insulator substrate that has been etched to form a serpentine valve seat microchannel structure (not shown) including at least one pressure sensor 155 and optionally a second pressure sensor 157. The second plate 152 is preferably an etched glass plate. The PAM throttle 150 also includes a piezoelectric material (e.g., a piezoelectric stack 156 as illustrated) external to the flow path 153 and in contact with the first plate 152. Preferably, the piezoelectric stack 156 is formed from lead zirconate titanate (PZT).

The PAM throttle 150 operates by pressing the first plate 154 against the second plate 152 using the piezoelectric stack 156. The spacing between the first and second plates 152, 154 (i.e., the gap width of the flow path 153) depends on the degree of deflection caused by the changing height of the piezoelectric stack 156, where the height of piezoelectric stack 156 depends on the voltage applied thereto. The deflection of PZT is well known and the gap width of the flow path 153 can be set to any intermediate value between the fully open gap width and zero (i.e., when the PAM throttle 150 is closed). For example, the PAM throttle 150 gap width can be set to any value in a range of 0 μm (closed) to 8 μm (fully open) for a device suitably sized for an adult human.

The PAM throttle 150 has the benefit of very low power consumption. The PZT material primarily consumes power only when the throttle 150 resistance is adjusted (i.e., the height of the piezoelectric stack 156 is changed). Low power consumption is ideal for use in implantable medical devices where the replacement of a battery requires major surgery. Another benefit of the PAM throttle 150 is its small size. For example, the entire PAM throttle 150 of a device for human implantation can be housed in a ceramic casing that is only 1.5 cm×1.5 cm×1 cm in size.

Device Control

The liquid delivery control module 180 includes several components (not individually shown) to regulate the operation of the liquid delivery apparatus 100 for example an electronic control system, a communication system, a variety of sensors, and a power supply (e.g., a battery) to power the foregoing systems.

The electronic control system is not particularly limited and generally includes a microprocessor electrically connected to certain components of the liquid delivery apparatus 100 and memory (e.g., non-volatile) to store various device operation programs, protocols, and data. For example, in the embodiment illustrated in FIGS. 1 and 2, the microprocessor is electrically connected to the PAM throttle 150 (i.e., to effect changes in the height of the piezoelectric stack 156 and control the flow rate of fluid exiting the reservoir 120) and to the pressure sensor 155 (i.e., to read and store instantaneous pressure readings for use in feedback control algorithms). In general, however, the microprocessor can be electrically connected to any actively controllable liquid metering unit 160 (e.g., a valve or pump having variable settings), pressure source 140 (e.g., an electrolytic fluid cell having a variable rate of bubble generation), and/or sensors used for feedback control/data analysis.

The communication system also is not particularly limited and can include a wired and/or (preferably) a wireless interface to the microprocessor. The communication system is preferably configured for two-way communication such that new and/or updated programs and instructions can be uploaded to the microprocessor and further such that any flow rate time series data and/or any other sensed data stored in the microprocessor memory can be downloaded to an external computer (i.e., external to the patient) for data analysis.

The specific sensors included in a given embodiment also are not particularly limited, covering a broad range of sensors capable of measuring parameters related to fluid delivery, environmental parameters related to the liquid delivery apparatus 100 itself, and parameters related to the patient. Common sensors related to fluid delivery include those for pressure (e.g., micromachined pressure sensors) and flow rate (e.g., electromagnetic flow sensors). Environmental sensors can include accelerometers (e.g., shock sensors), magnetic field sensors, and temperature sensors. Sensors used to monitor a patient's state can include pH sensors, glucose sensors, hormonal sensors (e.g., estrogen, testosterone); sensors for cancer-indicating proteins (e.g., prostate-specific antigen (PSA) for prostate cancer, carcino-embryonic antigen (CEA) for uterine cancer), serotonin sensors, and dopamine sensors. Preferred sensors for inclusion in the liquid delivery apparatus 100 include pressure sensors, flow sensors, and accelerometers.

In an embodiment, The liquid delivery apparatus 100 and its embedded sensors are integrated with power and control electronics in the liquid delivery control module 180. The components of the control module 180 are optimized for ease of integration while minimizing power consumption. Suitable commercially available products for use in the electronic subsystems of the control module 180 exist. The communication protocol is preferably a 433 MHz time-duplexed binary phase shift keying (BPSK) transmission scheme with power-saving modifications. For example, the default state of the communication system is a sleep state. The communication system occasionally "wakes up" from the sleep state to listen for a start transmission signal from an external device and reciprocates the start transmission signal with a return signal containing synchronization data. After synchronization, the external device is able to communicate information requests, re-programming (e.g., new flow rate and/or bolus delivery schedules, system self-test commands, post-deployment calibration or recalibration), patient-controlled bolus delivery commands, or an end-transmission signal to the microprocessor. Any number of information requests and re-programming commands can be placed before the end-transmission signal, and each is executed by the liquid delivery apparatus 100 upon reception. Once the end-transmission signal is received, the liquid delivery apparatus 100 responds with the values of the information requests and sends an end-transmission signal. Communication continues back and forth in this manner until the external device sends an end communication command, at which time the liquid delivery apparatus 100 returns to the sleep state.

Preferably, the liquid delivery pathway 110 contains one or more embedded pressure sensors to measure the pressure of fluids being delivered by the liquid delivery apparatus 100. In one embodiment, the sensor is a piezoresistive, micromachined pressure sensor. The very small size of the piezoresistive, micromachined pressure sensor permits a multiplicity of pressure sensors to be integrated into the liquid delivery apparatus 100. Preferably, at least one pressure sensor is located to measure the pressure of the fluid inside the reservoir 120. For example, as illustrated in FIG. 2, the pressure sensor 155 is embedded in the upstream portion of the PAM throttle 150 (i.e., near the inlet portion of the fluid flow path 153) to provide the pressure in the reservoir 120. Additionally, a pressure sensor can be located to measure the pressure drop of the fluid across the liquid metering unit 160. For example, as further illustrated in FIG. 2, the pressure sensor 157 is embedded in the downstream portion of the PAM throttle 150 (i.e., near the outlet portion of the fluid flow path 153) to provide the pressure drop across the PAM throttle 150. Such embedded sensors can provide feedback data on the time-dependent flow rate and total delivery volume that is currently unavailable in commercial pumps, as explained in more detail below.

Additionally, the liquid delivery apparatus 100 can contain an accelerometer to measure and record to acceleration forces experienced by the liquid delivery apparatus 100, which forces correspond to those experienced by a patient (i.e., when the liquid delivery apparatus 100 is implanted into the patient). A shock sensor is a suitable type of accelerometer, for example a micromachined device as described in U.S. Pat. No. 6,619,123 (the disclosure of which is incorporated herein by reference) that includes a plurality of shock sensors in an array to detect a plurality of different threshold acceleration forces. Commercially available accelerometers and algorithms of the kind often used in pedometers may be used, for example those available from Analog Devices, Inc. (e.g., ADXL models; Norwood, Mass.) and Freescale Semiconductor, Inc. (e.g., MMA models; Austin, Tex.). The accelerometers can then be used to determine an activity level of a patient having an implanted liquid delivery apparatus 100, for example by measuring the total linear distance traveled (e.g., by walking) over a specified time interval.

Alternate Embodiments

Figure 6A:
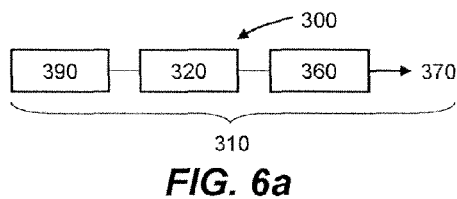
FIGS. 6*a* to 6*j* illustrate various alternative configurations of the general components of the disclosed liquid delivery apparatus.
Figure 6F:
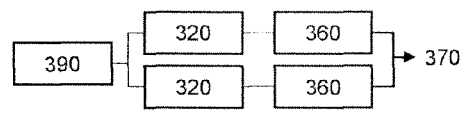
Figure 6B:
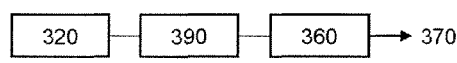
Figure 6G:
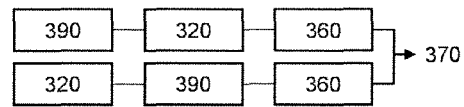
Figure 6C:
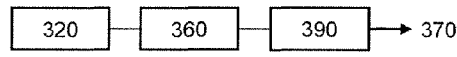
Figure 6H:
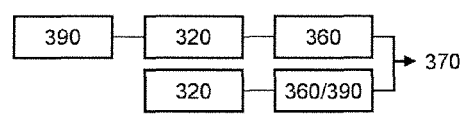
Figure 6D:
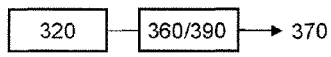
Figure 6E:
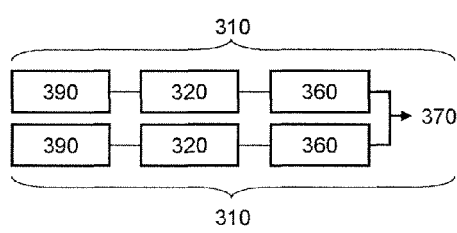
Figure 6I:
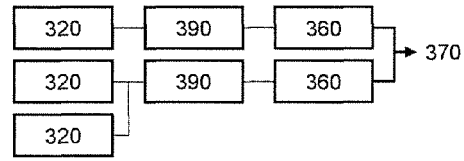
Figure 6J:
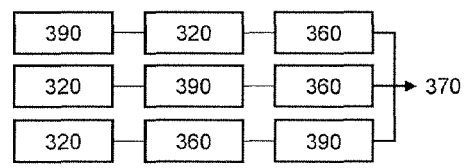

While the foregoing describes a particular embodiment of the disclosure as illustrated in FIGS. 1, 2, and 3a-3d, a variety of other arrangements of the general components described above is within the scope of the disclosure. For example, as illustrated in FIGS. 6a-6d, a general liquid delivery apparatus 300 includes a liquid delivery pathway 310 having a reservoir 320 fluidly connected to a liquid metering unit 360 fluidly connected to a catheter delivery tube 370 to deliver a fluid contained in the reservoir 320 to a patient when implanted. The reservoir 320, the liquid metering unit 360, and the catheter delivery tube 370 are analogous to the above-described components. However, the general liquid delivery apparatus 300 includes a force mechanism 390 that can be inserted into the flow line of the general liquid delivery apparatus 300 at a variety of locations, which force mechanism causes any fluid within the reservoir 320 to flow toward the catheter delivery tube 370 and into the patient. For example, when the force mechanism 390 is located upstream of the reservoir 320 (FIG. 6a), the force mechanism 390 can correspond to any of the above-described pressure sources 140 (e.g., a compressive sleeve spring, etc.) that provide a positive pressure to expel fluid from the reservoir 320. Similarly, when the force mechanism 390 is located upstream of the liquid metering unit 360 (FIG. 6b), downstream of the liquid metering unit 360 (FIG. 6c), or integrated with the liquid metering unit 360 (FIG. 6d), the force mechanism 390 can correspond to the above-described pumps associated with the liquid metering unit 160. Specifically, a force mechanism 390 that is discrete from the liquid metering unit 360 (FIGS. 6b and 6c) can be a pump that applies a certain suction pressure to the reservoir 320, while the liquid metering unit 360 (e.g., a PAM throttle) attenuates the flow rate to a desired value. Conversely, a force mechanism 390 that is integrated with the liquid metering unit 360 (FIG. 6d, illustrated as element "360/390") can be a positive displacement pump (e.g., aperistaltic pump) that can directly deliver and control the desired flow rate.

The single liquid delivery pathways 310 illustrated in FIGS. 6a-6d can be combined in parallel in a variety of ways to form dual (or higher) liquid delivery apparatus 300, of which FIGS. 6e-6j are non-limiting examples of a representative number of combinations. For example, FIG. 6e can correspond to the embodiment of FIG. 1, where the two force mechanisms 390 are compressive sleeve springs, the two reservoirs 320 include deformable balloons, and the two liquid metering units 360 are PAM throttles. Similarly, FIG. 6f can correspond to the embodiment of FIGS. 5a-5b, where the force mechanism 390 is a single compressive sleeve spring, the two reservoirs 320 are the two reservoir chambers of a partitioned single reservoir (i.e., and the force mechanism 390 ensleeves the partitioned single reservoir), and the two liquid metering units 360 are PAM throttles. The remaining embodiments of FIGS. 6g-6j are evident with reference to the foregoing discussion and the figures themselves.

Operation

The disclosed liquid delivery apparatus can be used in various modes of operation, for example to deliver drugs to a patient or to provide diagnostic information about a patient once implanted.

A preferred mode of operation includes the independent control and delivery of two or more different medications from two or more separate reservoirs to a patient. In this case, any of the above liquid delivery apparatus having two or more liquid delivery pathways and a microprocessor electrically connected to the flow-control structure of each liquid delivery pathway (e.g., a PAM throttle and a pressure sensor to measure reservoir volume) can be used. The reservoir(s) in each liquid delivery pathway is then charged with a medication such that at least one liquid reservoir contains a medication that is different from the medication contained in another liquid reservoir. Once implanted into a patient, the medications are delivered to the patient at independently controlled flow rates by independently controlling the flow-control structure of each liquid delivery pathway (e.g., by actuating the PAM throttle) in response to a flow control program stored in the microprocessor.

The specific medications delivered by the liquid delivery apparatus are not particularly limited. However, the use of a liquid delivery apparatus having two or more separate reservoirs is particularly useful when the medications to be delivered are incompatible/unstable in a mixture, or when it is desirable to adjust the relative delivery rates between the different medications. A preferred combination of medications includes at least one opioid and at least one non-opioid used for pain management. Suitable opioids include morphine, hydromorphone, fentanyl, sufentanil, meperidine, buprinorphine, and methadone. Suitable non-opioids include adenosine, baclofen, droperidol, gabapentin, ketorolac, midazolam, neostigmine, octreotide, and ziconotide. A particularly preferred opioid/non-opioid combination includes morphine and baclofen. Other suitable uses for the disclosed liquid delivery apparatus include the delivery of local anesthetics (e.g., bupivacaine, ropivacaine, tetracaine), adrenergic agonists (e.g., clonidine, moxonidine), N-methyl-D-aspartate (NMDA) antagonists (e.g., ketamine), chemotherapy drugs (e.g., hepatic artery infusion 5-fluorouracil ("5-FU"), melphalan, and/or cisplatinum), and antibiotics.

In the embodiment described in relation to FIGS. 1 and 2, the delivery flow rate of a fluid from the reservoir 120 can be controlled by measuring the reservoir 120 pressure. As illustrated in FIG. 4, the volume of fluid in the reservoir 120 is correlated with the reservoir 120 pressure. Accordingly, time series measurements of the reservoir 120 pressure (e.g., via the pressure sensor 155) can be converted to an equivalent time series of the reservoir 120 fluid volume, and the change in fluid volume over a specified measurement time interval ($\Delta V/\Delta t$) can be computed (e.g., using the microprocessor) to estimate the instantaneous fluid delivery flow rate. By computing the instantaneous fluid delivery flow rate, the microprocessor can then actuate the PAM throttle 150 to adjust the flow rate to a desired value, based on a program stored in the microprocessor. For example, it may be desirable to deliver: (1) a constant or substantially constant fluid flow rate over an indefinite period, (2) a fixed-volume bolus of fluid over a discrete period, or (3) combinations thereof. When a substantially constant fluid flow rate is desired, the pressure sensor 155 is used to constantly monitor the fluid flow rate; when the fluid flow rate drops below a specified value (i.e., due to the reduction in reservoir 120 pressure as the reservoir 120 empties), the microprocessor actuates and further opens the PAM throttle 150 so that it provides a lower resistance to flow, thereby increasing fluid flow rate back to a desired set point. When a fixed-volume bolus is desired, the initial reservoir 120 fluid volume can be measured using the pressure sensor 155, the PAM throttle 150 can be opened to release fluid, and the PAM throttle 150 can be subsequently closed once the reservoir 120 fluid volume has dropped by an amount corresponding to the desired fixed-volume bolus (i.e., as determined by ongoing pressure measurements).

The disclosed liquid delivery apparatus can also provide objective diagnostic information about a patient, for example by optimizing the dosage level of a plurality of medications to a patient during a titration stage of therapy. When a general multi-reservoir liquid delivery apparatus having an accelerometer is charged with two or more different medications and is implanted in the patient, the patient's activity levels over specific periods can be monitored to identify optimum dosage levels of each medication. Once the optimum dosage levels are determined, each of the medications can be delivered to the patient in combination and at their respective optimum levels to achieve the maximum therapeutic benefit with the minimum effective doses.

For example, when the liquid delivery apparatus contains a first and second medication, a first activity level of the patient is monitored to identify a first optimum dosage level of the first medication, and then a second activity level of the patient is monitored to identify a second optimum dosage level of the second medication. In this optimization context, a medication can be a single component or a blend of components (e.g., the first medication could be a blend of two opioids, while the second medication could be a single non-opioid). Both monitoring steps preferably include delivering only one medication to the patient at a plurality of dosage levels for a preselected length of time; using the accelerometer to measure and record the patient's activity at each of the dosage levels; and, then selecting the optimum dosage level based on the dosage level that provides the greatest activity level.

Figure 7A:
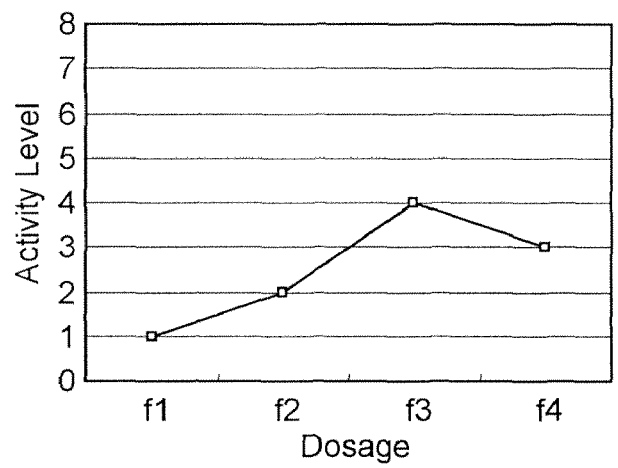
FIGS. 7*a* to 7*c* are graphs illustrating a method of optimizing the dosage level of a plurality of medications to a patient in need thereof.
Figure 7B:
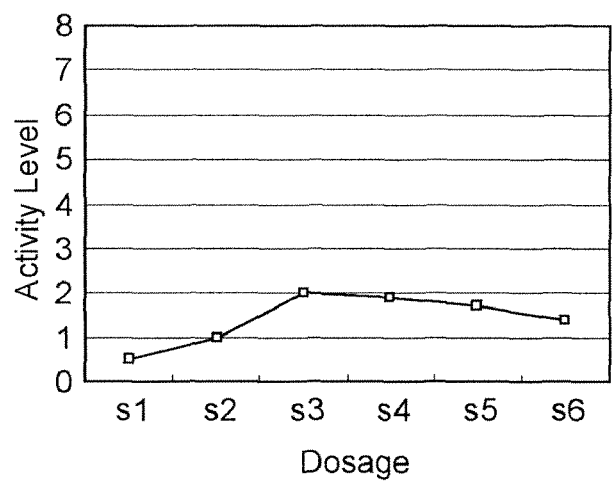
Figure 7C:
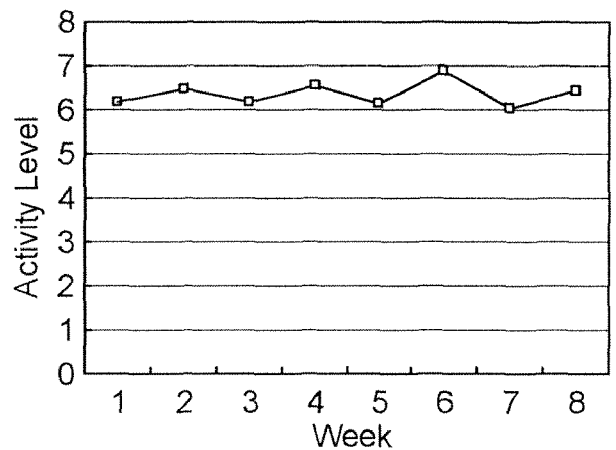

FIGS. 7a-7c illustrate hypothetical optimization and monitoring steps in more detail, for example when a patient's activity level is measured using the accelerometer in terms of the total distance the patient walks in successive one-week periods during which periods the dosage level of the delivered medication is substantially constant.

FIG. 7a illustrates the first monitoring step in which only the first medication (e.g., an opioid) is delivered to the patient at successively increasing, substantially constant dosages $f_1$, $f_2$, $f_3$, and $f_4$, where the dosages are altered at weekly intervals by a physician (or in response to a programmed dosage sequence in the microprocessor), generally at least until a local maximum in the activity level is identified. During the first monitoring step, the accelerometer constantly monitors and stores the patient's activity level, illustrated in FIG. 7a in arbitrary activity units (e.g., distance walked). Once patient activity data as a function of dosage level is obtained, the physician can tabulate, plot, or otherwise analyze the data to estimate the patient-specific optimum dosage level of the first medication (i.e., the dosage level at which the therapeutic benefit of the medication is maximized, prior to the onset of any debilitating effects from a medication overdose). As illustrated in FIG. 7a, $f_3$ is the estimated optimum dosage level of the first medication with an activity of 4 units. Depending on the interval spacing of the dosage test levels $f_1$, $f_2$, $f_3$, and $f_4$, it may be desirable to perform further monitoring steps for the first medication to more accurately estimate the optimum (i.e., by testing more dosage levels between $f_2$ and $f_4$ in the example illustrated in FIG. 7a).

FIG. 7b illustrates the analogous second monitoring step in which only the second medication (e.g., a non-opioid) is delivered to the patient at successively increasing, substantially constant dosages $s_1$, $s_2$, $s_3$, $s_4$, $s_5$, and $s_6$ over weekly intervals. As illustrated in FIG. 7b, $s_3$ is the estimated optimum dosage level of the first medication with an activity of 2 units.

Once the optima $f_3$ and $s_3$ are identified, the liquid delivery apparatus can be reprogrammed by the physician so that it simultaneously delivers the first medication at $f_3$ and the second medication at $s_3$. Once simultaneous delivery of the two medications is initiated, the patient's activity can be further monitored to verify that the two medications in combination provide an additive, net beneficial effect. As illustrated in FIG. 7c, the two medications can exhibit an additive, synergistic effect (i.e., the combination of medications results in an activity level of 6 or more units, which is at least as high as added activity levels of 4 units and 2 units resulting from the use of only a single medication). However, even if no synergistic effect is observed, the additional monitoring step can be performed to verify that at least some additive benefit is obtained by using the two medications in combination (i.e., to verify that the combination of medications results in an activity level of more than 4 units, which is greater than the use of any single medication alone).

EXAMPLE

Various components of the liquid delivery apparatus 100 according to the disclosure and as illustrated in FIGS. 1, 2, and 3a-3d were assembled and tested to determine their ability to reliably deliver independently controlled volumes of fluid.

A reservoir 120 was formed from a polyethylene terephthalate (PET) balloon 130 using a compressive sleeve spring 142 as a pressure source 140. The compressive sleeve spring 142 was made from a 45% cold-reduced Co/Ni/Cr ELGILOY alloy in a planar sheet. A metal compressive sleeve spring 142 was used because it is small, offers comparable pressures to traditional springs, and undergoes gradual degradation instead of critical failure. The compressive sleeve spring 142 was fabricated by laminating the sheet of ELGILOY alloy with a photoresist, patterning the photoresist, and then chemically etching the alloy to form the planar spring illustrated in FIGS. 3a and 3b (i.e., 100 µm thickness, 150 µm wide beams, with a mesh cell size of 600 µm by 6 mm). The etched planar sheet was then conditioned by stretching to a 100% elongation state, after which the etched, conditioned planar sheet had a repeatable spring constant of about 306 N/m. The etched, conditioned planar sheet was then rolled into a sleeve and the seams were epoxy bonded to form the compressive sleeve spring 142 illustrated in FIGS. 3c and 3d (i.e., a cylindrical sleeve about 60 mm long with about a 6 mm diameter). The PET balloon 130 had a length of about 60 mm and a diameter of about 20 mm when inflated (i.e., an inflated capacity of about 18.8 ml as compared to unpressurized volume of 4.7 ml). The PET balloon 130 was then inserted into the compressive sleeve spring 142 and inflated to a 20 mm diameter (FIG. 3d) with a liquid (water).

The relationship between the reservoir 120 volume and pressure is a calibration parameter used to control the volume of fluid delivered by the liquid delivery apparatus 100, whether as a fixed-volume bolus or over a period at a substantially constant flow rate. Tests were conducted in which the reservoir 120 was inflated with a liquid, and the resulting pressure and diameter of the reservoir 120 were monitored. The liquid was pressurized with nitrogen, and the reservoir 120 diameter was measured using micro-calipers. During inflation, the reservoir 120 diameter changed linearly, typically from about 12 mm to about 19 mm as the compressive sleeve spring 142 provided the pressurizing force. Beyond 19 mm, the elasticity of the PET balloon 130 changed the pressure generation curve. When fully inflated, the reservoir 120 generated about 15 kPa.

The gauge factor (ratio of fractional change in resistance to fractional change in length) for most bulk metals is 1-10. Thus, the ELGILOY alloy used to form the compressive sleeve spring 142 (or other piezoresistive material) could be used as a strain gauge to measure distention (i.e., and diameter as well) in the PET balloon 130. Such measurement of the diameter of the PET balloon 130 could be used in place of or in addition to the pressure sensor 155 as an additional method for determining the instantaneous volume of fluid contained in the reservoir 120.

A PAM throttle 150 substantially as described above and having a PZT piezoelectric stack 156 was fabricated for testing with the fabricated reservoir 120. The PAM throttle 150 was housed in a 1.5 cm×1.5 cm×1 cm ceramic casing and was capable of attaining a gap width ranging from 0 µm to 8 µm between the first and second plates 152, 154 of the PAM throttle 150. Actuation of the PAM throttle 150 to change the gap width from a first value to a second value in the 0 µm to 8 µm range could be performed at voltages up to 120 V and required 376.8 µJ per change (though a semi-empirical estimate of the required energy is about 9.2 mJ per charge). At rest, the PAM throttle 150 consumed about 34 nA or less. Thus, the total power consumption of the PAM throttle 150 is a combination of its continuous power draw and the added consumption of any actuation events.

The known characteristics of the reservoir 120 and the PAM throttle 150 allow multiple modes of flow regulation and allow the delivery of substantially constant flow rates based on a compromise between flow rate accuracy and power consumption of the liquid delivery apparatus 100.

As described and illustrated above, pressure (P), which is the pressure at the point of delivery, is generated as a continuous function of the volume (V) of the reservoir 120 (i.e., P=f(V); FIG. 4). The flow rate (Q) from the reservoir 120 is related to the differential pressure between the reservoir 120 and the delivery load through the hydraulic resistance of the serial combination of the PAM throttle 150 and the liquid delivery catheter 170. For an unactuated, open PAM throttle 150, the minimum hydraulic resistance is $7.32 \times 10^{12}$ Pa·s/m³ ($R_{Throttle}$), which is about 10 times the resistance for a 1 m catheter ($6.519 \times 10^{11}$ Pa·s/m³). Therefore, the hydraulic resistance of the PAM throttle 150 approximately defines the net hydraulic resistance of the liquid delivery apparatus 100 ($R_{System}$). Accordingly, the fluid delivery flow rate can be regulated by changing hydraulic resistance of the PAM throttle 150:

$$Q = \frac{P}{R_{System}} \approx \frac{P}{R_{Throttle}} = -\frac{\partial [f^{-1}(P)]}{\partial t}. \qquad \text{Eqn. (1)}$$

The flow rate is the change in volume with time and can be expressed as a function of pressure. Therefore, the delivery flow rate can be determined by monitoring the change in reservoir pressure over time using the pressure sensor 155. Such a control mechanism requires no information about the PAM throttle 150 for accurate flow regulation, and it can be used to regulate a fixed-volume bolus delivery from the reservoir 120. For the tested PAM throttle 150, the highest possible actuation voltage was 120 V, which resulted in a flow rate of 5.0 ml/day and required a minimum pressure difference (ΔP) of 130 Pa.

Another control mechanism involves setting the PAM throttle 150 to a fixed gap width and periodically opening it further to maintain a set flow rate as the reservoir 120 pressure drops. For a particular PAM throttle 150 set point, the hydraulic resistance is constant. As indicated in Eqn. 1, the flow rate is the reservoir 120 pressure divided by the hydraulic resistance, and the reservoir 120 pressure changes as material flows from it, so the flow rate for a particular set point is a function of time:

$$Q = Q_{set} + Q_{err} = \frac{P(t)}{R_{Throttle}} = h(t). \quad \text{Eqn. (2)}$$

For a constant PAM throttle 150 set point, there is a set flow rate ($Q_{set}$) and an acceptable deviation from this set point ($Q_{err}$) such that the flow rate remains within an acceptable error range. The flow rate function h(t) will slowly decay because the reservoir 120 pressure drops as it empties. The initial time ($t_a$) and the final time ($t_b$) that the flow rate will be within the error bounds for a particular set point can be determined:

$$t_a = h^{-1}(Q_{set} + Q_{err}); \ t_b = h^{-1}(Q_{set} - Q_{err}) \quad \text{Eqn. (3)}$$

Thus, given a desired set flow rate ($Q_{set}$) and accuracy level ($Q_{err}/Q_{set}$; e.g., about 10% or less, preferably about 5% or less, 1% or less, or 0.2% or less), the time interval ($t_a$-$t_b$) over which the PAM throttle 150 can remain in a given state can be determined; this time interval similarly dictates the frequency with which the PAM throttle 150 is actuated to obtain a substantially constant flow rate.

Figure 8:
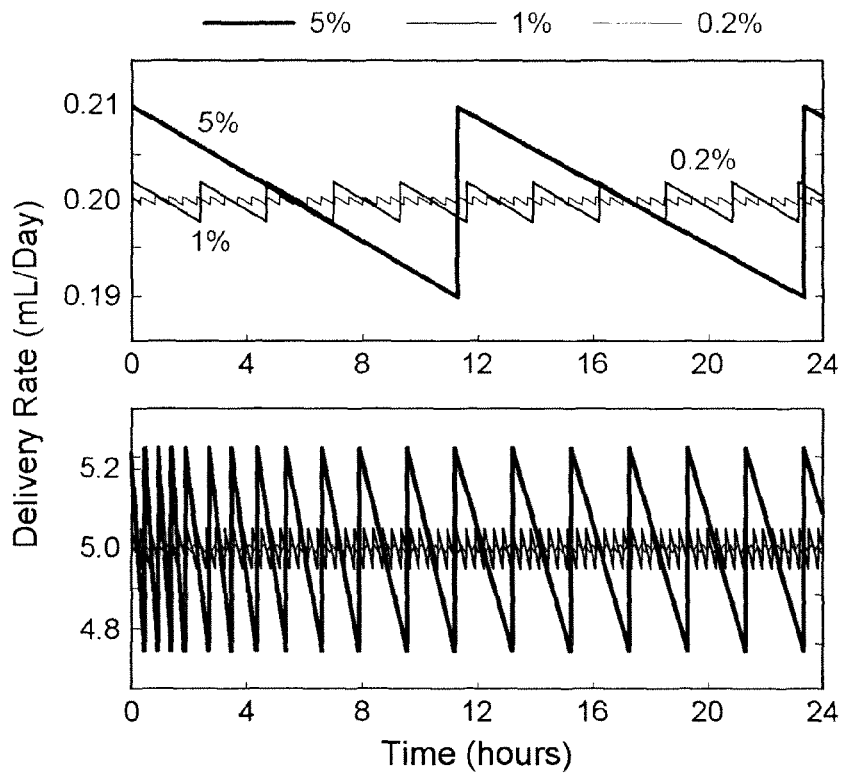
FIG. 8 is a graph illustrating the actuation frequency of a piezoelectrically actuated microvalve throttle as a function of the accuracy of the fluid flow rate delivered by the liquid delivery apparatus of FIG. 1.

For example, the typical range of delivery for intrathecal morphine varies from about 0.2 ml/day to about 5.0 ml/day. Analytical models based on empirical data from the PAM throttle 150 and the reservoir 120 with the compressive sleeve spring 142 were used to simulate drug delivery from the liquid delivery apparatus 100 at various constant flow rates. FIG. 8 illustrates the results of these simulations at varying error rates over one day (i.e., $Q_{err}/Q_{set}$=5%, 1%, and 0.2%). The actuated frequency for delivering 0.2 mL/day with a 5% error is 2.1 adjustments/day (FIG. 8, top). The primary power draw at such a switching frequency is the leakage through the PAM throttle 150. Conversely, the highest computed power consumption scenario requires one adjustment every four minutes to regulate 5.0 mL/day with 0.2% accuracy (FIG. 8, bottom), and the resulting power draw of the PAM throttle 150 is 1.68 µW. Thus, the disclosed liquid delivery apparatus 100 is flexible in that it can operate very energy-efficiently when high levels of accuracy are not required; conversely, it is capable of operating at high levels of accuracy when needed, albeit at the cost of increased energy consumption.

Figure 9:
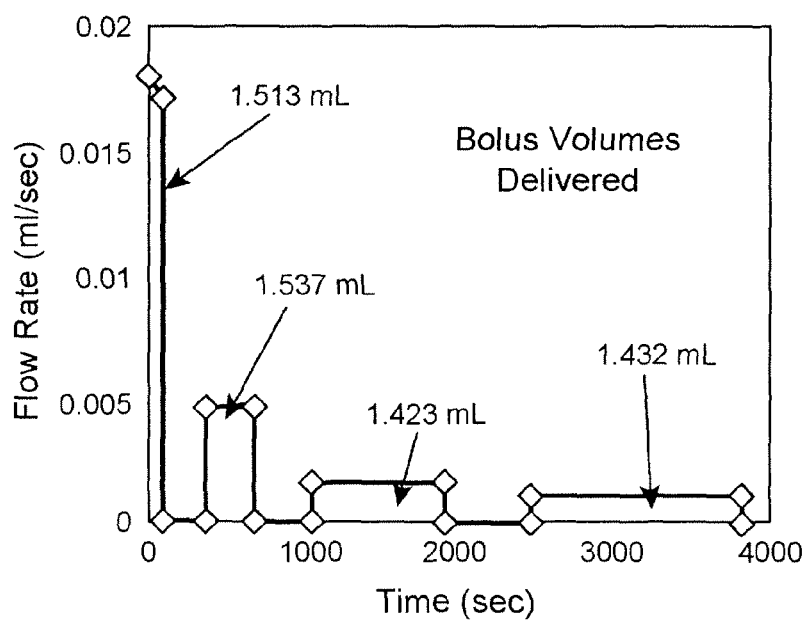
FIG. 9 is a graph illustrating the accuracy of a fixed-volume bolus delivered by the liquid delivery apparatus of FIG. 1.

The fabricated combination of the PAM throttle 150 and the reservoir 120 was also tested to characterize the ability of the combination to reliably deliver fixed-volume bolus doses of fluid. Because the progressive reduction of the reservoir 120 pressure accompanies the delivery of any volume of fluid, and further because the relation between pressure and volume is known, a bolus regulation program can calculate the PAM throttle 150 aperture and timing based on pressure measurements. For example, the PAM throttle 150 is opened to begin bolus delivery, and after the prescribed pressure drop that corresponds to the desired fixed bolus volume is observed, the valve is closed. FIG. 9 illustrates a delivery of 6 ml over four 1.5 ml bolus doses. The initial volume is determined using inlet pressure, and the stop pressure is calculated from the reservoir 120 pressure-volume relationship. From FIG. 9, it is apparent that a liquid delivery apparatus using the PAM throttle 150 and the reservoir 120 is capable of accurately delivering a specified fixed-volume bolus of fluid, regardless of whether the delivery time is on the order of about $10^2$ s or about $10^3$ s.

A liquid delivery apparatus 100 constructed from the fabricated PAM throttle 150 and reservoir 120 would be both compact and volume-efficient. For example, an external housing having a total volume of 73.9 ml (8.8 cm×4.8 cm×1.75 cm) has sufficient space for two liquid delivery paths 110 (i.e., each requiring 18.8 ml for the reservoir 120 and 2.25 ml for the PAM throttle 150) and enough additional space for a liquid delivery control module 180 including a microprocessor, circuitry, a battery, etc. The volume efficiency and estimated weight of such a device is 0.51 (i.e., 2×18.8 ml/73.9 ml) and about 80 g. As illustrated in Table 1, the disclosed liquid delivery apparatus 100 is (1) more compact and volume-efficient than commercially available intrathecal pumps and (2) more versatile that the commercially available intrathecal pumps (i.e., because they only provide single-reservoir devices). Further, the disclosed liquid delivery apparatus is energy efficient relative to other battery-powered devices, such that conventional battery technology used in the disclosed device can power the device at least about 2 to 3 times longer than a battery-powered commercially available intrathecal pump. In Table 1, multiple columns for a single device indicate the commercially available range of sizes for a particular model.

TABLE 1

Comparison of Disclosed Liquid Delivery Apparatus with Commercially Available Intrathecal Pumps

| Device | Disclosed Device | Medtronic SYNCHROMED EL | | Medtronic ISOMED | | | Codman CODMAN 3000 | | |
|---|---|---|---|---|---|---|---|---|---|
| Reservoir Type | Dual | Single | | Single | | | Single | | |
| Device Volume (ml) | 73.9 | 123 | 157 | 112 | 135 | 172 | 94.1 | 162 | 219 |
| Reservoir Vol. (ml) | 2 × 18.8 | 10 | 18 | 20 | 35 | 60 | 16 | 30 | 50 |
| Volume Efficiency | 0.509 | 0.081 | 0.115 | 0.178 | 0.259 | 0.348 | 0.170 | 0.185 | 0.228 |
| Device Weight (g) | 80 | 185 | 205 | 113 | 116 | 120 | 98 | 137 | 173 |
| Battery Life (yr) | 15+ | 5 to 7 | | No battery | | | No battery | | |
| Flow Rates (ml/day) | 0.1 to 30 (each; programmable) | 0.5 to 20 (programmable) | | 0.3, 0.5, 1.0, 1.5, 4.0 (constant flow) | | | 0.3, 0.5, 1.0, 1.7 (constant flow) | | |

In view of the foregoing, the disclosed liquid delivery apparatus possesses several advantages relative to conventional intrathecal pumps. Regardless of whether the liquid delivery apparatus is configured with a single fluid reservoir or two or more fluid reservoirs, the disclosed apparatus is highly compact, volume-efficient, and energy-efficient. Similarly, the liquid delivery apparatus having any number of reservoirs is capable of accurately delivering fluid (1) at constant or substantially constant flow rates and/or (2) as a fixed-volume bolus. When the liquid delivery apparatus includes two or more fluid reservoirs, the fluid flow rate from each reservoir can be independently controlled, and potential complications due to medication incompatibilities can be avoided. Further, the inclusion of two or more fluid reservoirs permits an optimization of the dosage level for different medications in each of the reservoirs.

Because other modifications and changes varied to fit particular operating requirements and environments will be apparent to those skilled in the art, the invention is not considered limited to the example chosen for purposes of disclosure, and covers all changes and modifications which do not constitute departures from the true spirit and scope of the invention.

Accordingly, the foregoing description is given for clearness of understanding only, and no unnecessary limitations should be understood therefrom, as modifications within the scope of the invention may be apparent to those having ordinary skill in the art.

Throughout the specification, where the compositions, processes, or apparatus are described as including components, steps, or materials, it is contemplated that the compositions, processes, or apparatus can also comprise, consist essentially of, or consist of, any combination of the recited components or materials, unless described otherwise. Combinations of components are contemplated to include homogeneous and/or heterogeneous mixtures, as would be understood by a person of ordinary skill in the art in view of the foregoing disclosure.

What is claimed is:

1. A liquid delivery apparatus comprising a liquid delivery pathway, the liquid delivery pathway comprising:
    a liquid reservoir comprising a deformable balloon and a pressure source selected from the group consisting of a compressive sleeve spring and an electrolytic fluid cell;
    a liquid metering unit comprising a throttle, the liquid metering unit fluidly connected to the liquid reservoir;
    a pressure sensor fluidly connected to the liquid reservoir between the liquid reservoir and the liquid metering unit throttle; and,
    a catheter delivery tube fluidly connected to the liquid metering unit.

2. The liquid delivery apparatus of claim 1, wherein the liquid reservoir further comprises a refill port.

3. The liquid delivery apparatus of claim 1 further comprising a bolus port fluidly connected to the catheter delivery tube.

4. The liquid delivery apparatus of claim 1, wherein the pressure source is an electrolytic fluid cell.

5. The liquid delivery apparatus of claim 1 further comprising a liquid delivery control module, the liquid delivery control module comprising:
    a microprocessor electrically connected to the throttle and the means for measuring the volume of the liquid reservoir; and,
    a battery electrically connected to the microprocessor.

6. The liquid delivery apparatus of claim 5, comprising a plurality of liquid delivery pathways, wherein the microprocessor is capable of independently controlling liquid flow through each liquid delivery pathway.

7. The liquid delivery apparatus of claim 1 further comprising a plurality of liquid delivery pathways.

8. The liquid delivery apparatus of claim 7, comprising a liquid delivery catheter fluidly connected to the catheter delivery tube of each of the plurality of liquid delivery pathways.

9. The liquid delivery apparatus of claim 1, wherein the pressure source is a compressive sleeve spring comprising a piezoresistive material.

10. The liquid delivery apparatus of claim 9, wherein the compressive sleeve spring comprises a Co/Cr/Ni alloy.

11. The liquid delivery apparatus of claim 1, wherein the throttle comprises a piezoelectrically actuated microvalve.

12. The liquid delivery apparatus of claim 11, wherein the piezoelectrically actuated microvalve comprises:
    a first plate and a second plate spaced apart and joined together to define a flow path having an inlet fluidly connected to the liquid reservoir and an outlet fluidly connected to the catheter delivery tube; and,
    a piezoelectric material external to the flow path and in contact with the first plate.

13. The liquid delivery apparatus of claim 12, wherein:
the first plate comprises a silicon-on-insulator substrate;
the second plate comprises glass; and,
the piezoelectric material comprises lead zirconium titanate.

14. A liquid delivery apparatus comprising:
    a liquid reservoir comprising a deformable balloon having an interior volume and at least one deformable interior wall in the interior volume, the at least one deformable interior wall defining a plurality of reservoir chambers in the interior volume;
    a plurality of liquid metering units, each of which is fluidly connected to one of the reservoir chambers;
    a at least one pressure sensor fluidly connected to at least one of the reservoir chambers between the reservoir chamber and the corresponding liquid metering unit; and,
    a plurality of catheter delivery tubes, each of which is fluidly connected to one of the liquid metering units.

15. The liquid delivery apparatus of claim 14 further comprising a liquid delivery catheter connected to each of the catheter delivery tubes.

16. The liquid delivery apparatus of claim 14, wherein the liquid reservoir further comprises a refill port.

17. The liquid delivery apparatus of claim 14 further comprising a plurality of bolus ports, each of which is fluidly connected to one of the catheter delivery tubes.

18. The liquid delivery apparatus of claim 14, wherein
    the liquid reservoir further comprises a pressure source selected from the group consisting of a compressive sleeve spring, a torsion spring, and an electrolytic fluid cell; and
    each liquid metering unit comprises a throttle.

19. The liquid delivery apparatus of claim 18, wherein the pressure source is a torsion spring.

20. The liquid delivery apparatus of claim 18, wherein the pressure source is an electrolytic fluid cell.

21. The liquid delivery apparatus of claim 18, further comprising a liquid delivery control module, the liquid delivery control module comprising:
    a microprocessor electrically connected to the throttle and the means for measuring the volume of the liquid in the reservoir chambers; and
    a battery electrically connected to the microprocessor.

22. The liquid delivery apparatus of claim 21, wherein the microprocessor is capable of independently controlling liquid flow through each throttle.

23. The liquid delivery apparatus of claim 18, wherein the pressure source is a compressive sleeve spring.

24. The liquid delivery apparatus of claim 23, wherein the compressive sleeve spring comprises a Co/Cr/Ni alloy.

25. The liquid delivery apparatus of claim 18, wherein the throttle comprises a piezoelectrically actuated microvalve.

26. The liquid delivery apparatus of claim 25, wherein the piezoelectrically actuated microvalve comprises:
   a first plate and a second plate spaced apart and joined together to define a flow path having an inlet fluidly connected to the liquid reservoir and an outlet fluidly connected to the plurality of the catheter delivery tubes; and,
   a piezoelectric material external to the flow path and in contact with the first plate.

27. The liquid delivery apparatus of claim 26, wherein:
   the first plate comprises a silicon-on-insulator substrate;
   the second plate comprises glass; and,
   the piezoelectric material comprises lead zirconium titanate.

28. A method of delivering a plurality of medications to a patient in need thereof, the method comprising:
   providing the liquid delivery apparatus of claim 7, the apparatus further comprising a microprocessor electrically connected to the throttle and the pressure sensor;
   charging the liquid delivery apparatus with the plurality of medications, wherein at least one liquid reservoir contains a medication that is different from the medication contained in another liquid reservoir; and,
   delivering the plurality of medications to the patient at independently controlled flow rates by independently actuating the throttle of each liquid delivery pathway in response to a flow control program stored in the microprocessor.

* * * * *